United States Patent [19]

Markowitz

[11] 4,344,437

[45] Aug. 17, 1982

[54] PACEMAKER TRIGGERING COUPLING CIRCUIT

[75] Inventor: H. Toby Markowitz, Anoka, Minn.

[73] Assignee: Medtronic, Inc., Minneapolis, Minn.

[21] Appl. No.: 145,051

[22] Filed: Apr. 30, 1980

[51] Int. Cl.³ ............................................... A61N 1/30
[52] U.S. Cl. .............................................. 128/419 PG
[58] Field of Search ................................... 128/419 PG

[56] References Cited

U.S. PATENT DOCUMENTS

| | | |
|---|---|---|
| 3,903,897 | 9/1975 | Woollons et al. |
| 4,038,991 | 8/1977 | Walters ........................ 128/419 PG |
| 4,059,116 | 11/1977 | Adams ........................ 128/419 PG |
| 4,060,090 | 11/1977 | Lin et al. ..................... 128/419 PG |
| 4,091,817 | 5/1978 | Thaler . |

FOREIGN PATENT DOCUMENTS 2701104  7/1978  Fed. Rep. of Germany .

Primary Examiner—William E. Kamm
Attorney, Agent, or Firm—Merchant, Gould, Smith, Edell, Welter & Schmidt

[57] ABSTRACT

An improved atrial synchronous pacemaker and control circuit therefor having a minimum ventricular rate backup mode includes circuitry for preventing occurrence of a closely coupled ventricular pulse which might otherwise occur during the vulnerable repolarization period of the ventricles. A triggering coupling circuit includes a variable or programmable upper rate limit/minimum escape interval timer and switching means therefor for switching to a relatively low maximum rate/minimum escape interval condition while pacing in the ventricular backup mode, and for switching to a higher programmed maximum rate/minimum escape interval limit value while pacing in atrial synchronous mode.

7 Claims, 5 Drawing Figures

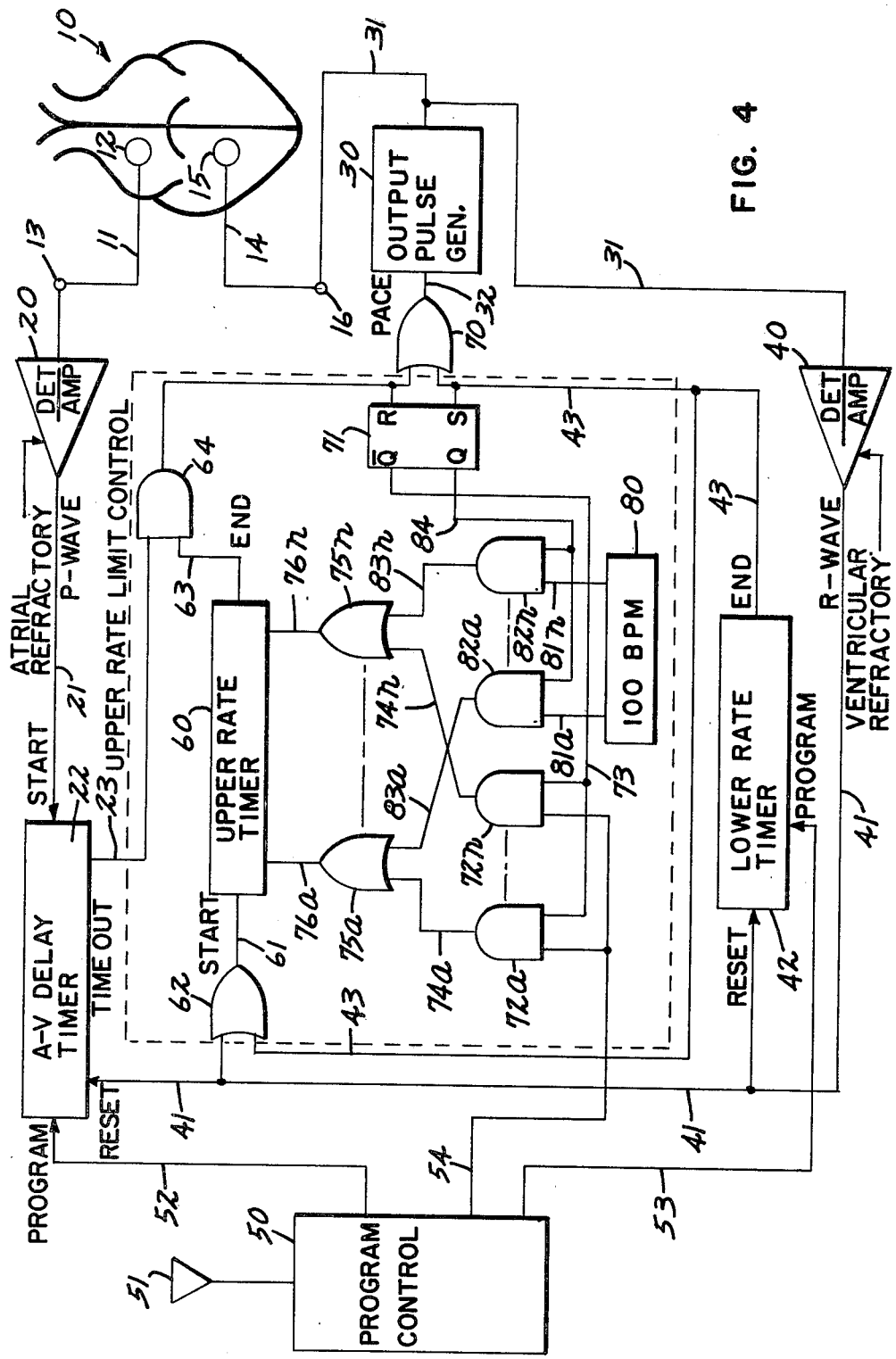

PACEMAKER TRIGGERING COUPLING CIRCUIT

TECHNICAL FIELD OF THE INVENTION

This invention pertains generally to the field of electrical heart pacemakers and control circuits therefor, and more specifically to improvements in triggering circuits for pacemakers having an atrial synchronous mode and a minimum rate ventricular backup mode, to prevent closely-coupled output pulses from falling in the vulnerable periods of the ventricles.

BACKGROUND OF THE PRIOR ART

Atrial synchronous pacemakers are designed for use on patients whose hearts have normal atrial self-pacing, but, due to a defect in the conduction from the atrium to the ventricle, the ventricles fail to beat or keep pace with the atrial rhythm. Atrial synchronous pacemakers are designed to sense the naturally occurring atrial contractions of the heart, and to use them as a timing reference for generating electrical stimulation pulses to the ventricle of the heart. This is done by sensing the atrial contraction and providing a ventricular stimulation pulse after a short time delay which is selected to give atrial-ventricular synchrony. Usually a ventricular sensing and inhibit mode is also provided in the pacemaker, so that if a spontaneous ventricular contraction does take place within the A-V time interval following an atrial contraction, the ventricular contraction will be sensed and the pulse generating circuits inhibited and reset for that heartbeat cycle, since no ventricular stimulating pulse is required.

It is also common to provide backup (minimum rate) ventricular pacing in an atrial synchronous pacemaker, so that the heart will be maintained at the minimum rate in the event that the natural atrial contraction rate drops too low as in the case of atrial bradycardia. Also, in the case of a malfunction of the atrial lead or atrial sensing amplifier, it is important that the pacemaker continue to pace in the ventricular backup mode.

A problem sometimes occurs in prior art atrial synchronous pacemakers when operating in the minimum rate ventricular backup maode, in that under certain circumstances it is possible that the pacemaker may deliver a ventricular stimulating pulse too rapidly after a previous ventricular contraction. This too-close coupling of a stimulation pulse may fall in the vulnerable period of the ventricles during repolarization from the previous ventricular contraction, and may lead to dangerous consequences, including ventricular fibrillation. Also, under those circumstances the electrocardiogram might easily be misunderstood by medical personnel as a malfunctioning pacemaker.

The cause of this problem is the dissociation of atrial and ventricular activity in the heart during the ventricular backup mode, and the subsequent sensing of an atrial contraction (P-wave) occurring very closely after a ventricular event. This may occur in the case of atrial bradycardia wherein the natural atrial rate drops to a rate which is below the minimum ventricular backup rate, which, for example, might be 60 beats per minute. Under those circumstances the ventricle of the heart is paced at the 60 beat per minute ventricular backup rate, but assuming no retrograde conduction in the heart, the atrium continues to self-pace at its lower rate. With the atria and ventricles now operating independently and at different frequencies, the P-wave of the electrocardiogram is no longer fixed or synchronized with the QRS-wave complex. On successive pulses, the P-wave will drift into and through the QRS complex. Eventually a P-wave will occur just as the atrial sensing amplifier is turned on at the end of its refractory period following a ventricular event, or very shortly thereafter. The atrial sensing amplifier will then detect the P-wave and cause delivery of a ventricular stimulation pulse. The pulse may be delivered one A-V delay period later or may be constrained by a rate limit circuit. The result in either case is that the ventricle is supplied with a rapid ventricular stimulation pulse after too short a time interval following the previous ventricular contraction, and this rapid stimulation pulse may fall in the vulnerable period.

It is not practical to solve the above problem by further lengthening the refractory period of the atrial sensing circuit. Although to do so would safely move the quickest sensed P-wave to beyond the vulnerable period following a ventricular depolarization, such a scheme would effectively lower the maximum atrial tracking rate limit of the pacemaker. This is a poor result because many patients with the type of problem requiring an atrial synchronous pacemaker may still exercise normally and reach heart rates in excess of 150 beats per minute. However, with a lengthened atrial refractory period, the atrial sensing circuits would not be ready to receive every P-wave at these rapid normal heart rates.

It is possible to avoid the above-noted problem of too closely coupled pulses through the use of a dual sense/dual pace atrial-ventricular pacemaker. That type of device is not subject to the same problem, because the atrium is paced to maintain the minimum rate, which keeps both the atria and ventricles synchronized. Therefore, dissociation of the P and R-waves does not occur. While a dual sense/dual pace pacemaker solves this problem, it may use considerably more current than an atrial synchronous pacemaker, and therefore is subject to the disadvantage of shortened battery life or larger size. A need therefore remains for atrial synchronous pacemakers, for those patients in which full dual sense/dual pace atrial-ventricular synchronous pacing is not needed.

The present invention solves the above problem by providing a variable upper rate limit, and providing sensing means for switching to the upper, normally high limit (which is programmable and typically may be 150 beats per minute) during atrial synchronous pacing, and for automatically switching to a lower upper rate limit (for example 100 beats per minute) when operating in the backup ventricular pacing mode. When atrial synchrony is regained, the upper rate limit is automatically returned to the higher programmed value. In this manner the atrial sensing circuit is effectively prevented from sensing a P-wave immediately following an R-wave, while at the same time atrial synchronous operation at high heart rates during exercise is not precluded.

SUMMARY OF THE INVENTION

According to the present invention there is provided an improved heart pacemaker and control circuits therefor having atrial synchronous and minimum rate ventricular backup pacing modes. A triggering coupling circuit is provided for preventing a ventricular stimulation pulse following too closely on a previous ventricular contraction. The pacemaker includes atrial and ventricular terminals for connecting respectively to the atrium and ventricle of the patient's heart. Output pulse generating means are provided for selectively delivering ventricular electrical stimulation output pulses to the ventricular terminal. Atrial and ventricular sense amplifier means are provided connected respectively to the atrial and ventricular terminals, for sensing, respectively, atrial and ventricular contractions of the heart. Control means are provided for normally triggering the pulse generating means to deliver output pulses synchronized with and delayed from sensed atrial contractions occurring faster than a predetermined minimum rate, and for causing the output pulse generating means to provide output pulses to maintain the ventricular rate of the heart at the predetermined minimum rate in the absence of sensed atrial contractions occurring at above the minimum rate. The control means further includes means for preventing delivery of an output pulse at a pacing rate in excess of a predetermined maximum pacing rate with respect to the preceding spontaneous or stimulated ventricular contraction. Further control means are included for increasing the predetermined maximum pacing rate limit during atrial synchronous pacing and for reducing the predetermined maximum pacing rate to a lower limit when pacing at the predetermined minimum pacing rate.

BRIEF DESCRIPTION OF THE DRAWING

In the drawing,

FIG. 4 is a block diagram of a pacemaker according to the present invention.

DETAILED DESCRIPTION OF THE PROBLEM

Figure 1:
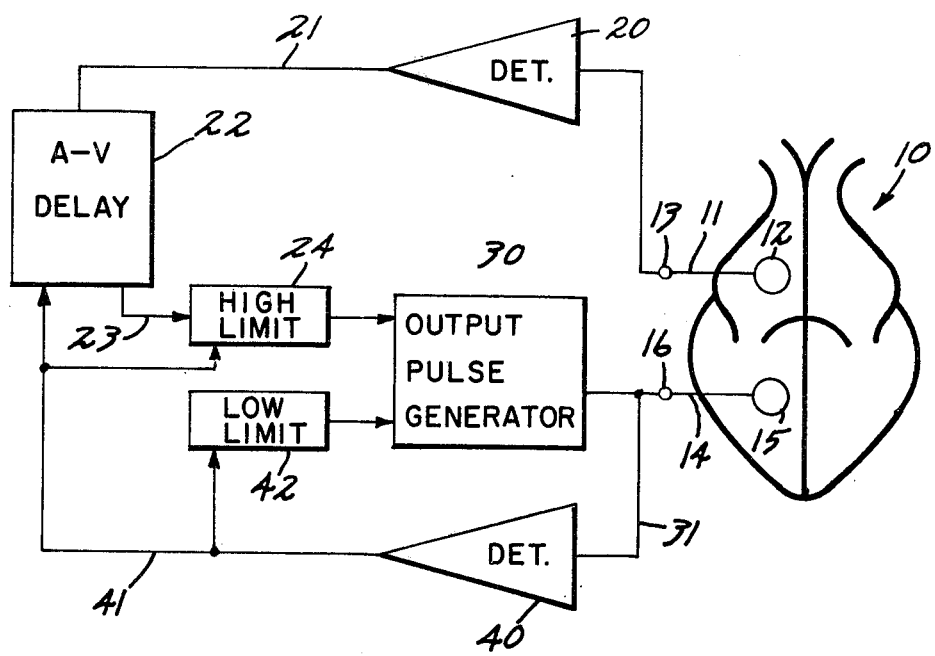
FIG. 1 is a block diagram of a atrial synchronous pacemaker having a ventricular backup pacing rate.
Figure 2:
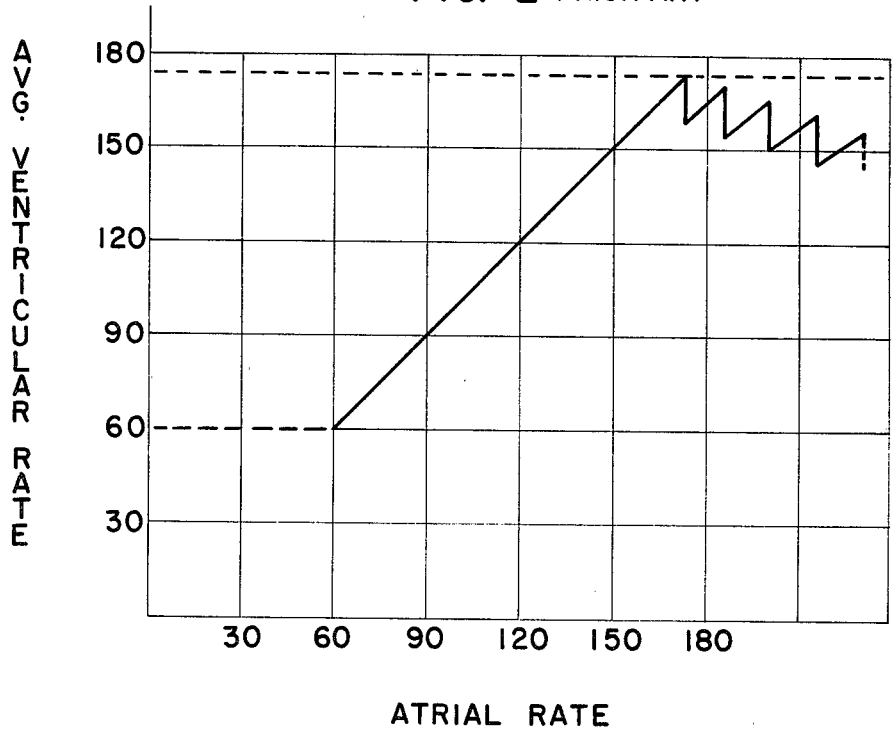
FIG. 2 is a graph illustrating the characteristic of average output stimulation rate versus atrial rate of operation of a pacemaker as in FIG. 1.

FIGS. 1 and 2 generally illustrate a P-wave synchronous, or, atrial synchronous pacemaker having a minimum ventricular rate backup pacing feature. The present invention is of the general type as shown in FIG. 1 and FIG. 2, but the present invention contains special means not specifically shown in FIG. 1 or 2, which solve the problem referred to previously of closely coupled ventricular stimulation pulses. The specific means provided in the present invention for solving this problem are discussed below with reference to FIGS. 4 and 5.

In FIG. 1, reference number 10 generally designates a heart with which the pacemaker is used. A lead 11 extends to the atrium of the heart and includes an electrode 12 in contact therewith. Electrode 11 extends to the atrial terminal 13 of the pacemaker. Lead 14 extends to the ventricle of the heart, and includes an electrode 15 at its end in contact with the tissues in the ventricle of the heart. Lead 14 extends to and connects the ventricular to terminal 16 of the pacemaker.

Within the pacemaker, terminal 13 connects to an atrial sense amplifier and detector 20, which functions to detect atrial depolarizations (P-waves). Its output on conductor 21 connects to an input of an atrial-ventricular delay timer 22. The trigger output of timer 22 connects via conductor 23 to a high rate limit timer 24. The output of this timer connects to output circuit 30. Ventricular stimulating pulses generated by output circuit 30 are delivered through conductor 31 to terminal 16 and to the ventricle of the heart.

A branch of conductor 31 connects to a ventricular sensing amplifier and detector 40, which functions to detect R-waves indicative of ventricular contractions, although it also responds to generated stimulating pulses from the output circuit. The output of ventricular sensing amplifier 40 connects over conductor 41 to reset inputs on A-V timer 22 and high rate limit timer 24. A branch also connects to a reset input of low rate limit timer 42. The output of this timer also connects to output circuit 30.

FIG. 2 shows the ventricular pacing rate that will be maintained by the pacemaker of FIG. 1, in response to varying atrial heartbeat rates. For illustrative purposes in FIG. 2, 175 beats per minute has been shown as the upper rate limit, and 60 beats per minute has been shown as the lower rate limit. It will be appreciated, however, that other numerical values could be used for these limits, and further that in the case of programmable pacemakers, these limits, as well as other operating parameters of the device, can be programmed through an rf transmission and programming technique as is known in the art.

In the example of FIG. 2, when the spontaneous atrial pacing rate of the heart is between 60 and 175 beats per minute, the ventricular rate matches the atrial rate on a one to one basis. In this region the pacemaker is operating in P-wave synchronous operation. The P-wave from an atrial contraction is picked up on lead 11 and sensed by amplifier 20 which then triggers timer 22, which times out the proper atrial-ventricular time delay, at the end of which a triggering pulse is sent over conductor 23. If this triggering pulse does not occur at too close an interval from the last ventricular event, it is passed through timer 24 to trigger the generation of an output stimulating pulse by circuit 30. Thus, a stimulated ventricular contraction occurs in synchrony with the spontaneous atrial contraction. If, prior to delivery of the ventricular stimulating pulse, a spontaneous ventricular contraction occurs, it would be sensed by amplifier 40, and a reset signal appearing at conductor 41 would reset timers 22, 24, and 44 to inhibit a ventricular pulse, since none is needed. In either case, the one to one correspondence between ventricular rate and atrial rate is maintained, with A-V synchrony.

If the atrial rate drops below the lower limit which is 60 beats per minute in the example of FIG. 2, P-wave synchronous pacing would result in a low heart rate. Therefore, below 60 beats per minute, the pacemaker reverts to ventricular demand pacing at the lower rate limit.

This is accomplished through the use of low rate limit timer 42, or equivalent structure. Upon each ventricular event, either a spontaneous contraction or a stimulation pulse, timer 42 is reset by a signal on conductor 41. It then begins timing out its time limit corresponding to the escape interval between beats at the lower limit rate. In the case of a 60 beat per minute lower limit, the time-out interval is 1,000 milliseconds. If timer 42 times out this interval, it will trigger output circuit 30 to deliver a stimulating pulse. If a naturally occurring ventricular contraction occurs prior to the time-out interval, timer 42 will be reset.

Figure 3:
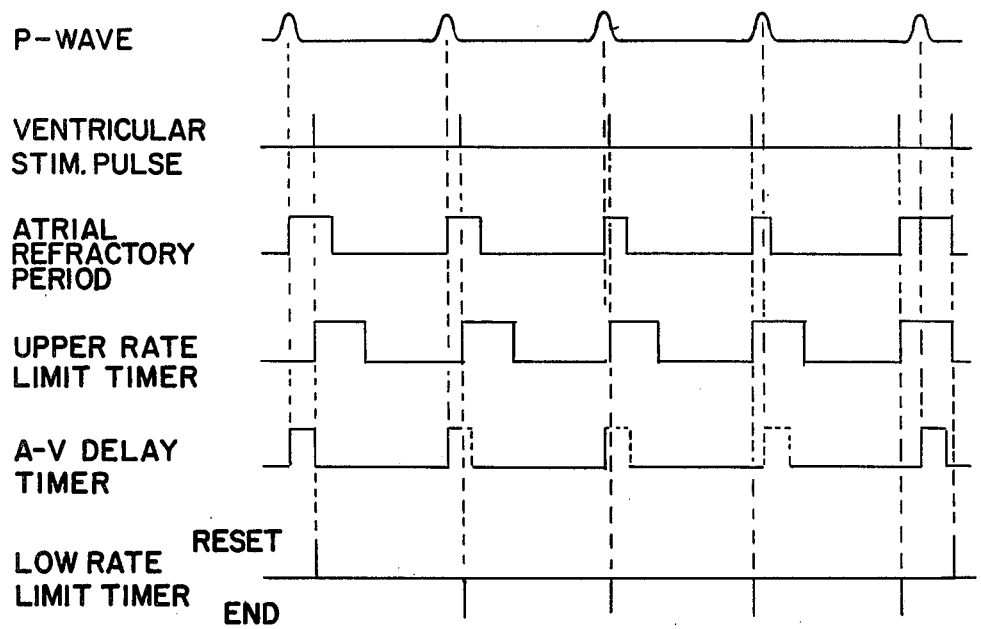
FIG. 3 is a timing chart illustrating a problem existing in prior art pacemakers involving closely coupled ventricular stimulation pulses.

The problem of too close coupling between ventricular stimulating pulses that exists in the prior art is illustrated in the timing chart of FIG. 3. In FIG. 3 the horizontal axis represents time, and six pertinent parameters showing the functioning of the heart and the pacemaker are shown, as labeled in the figure. The top line shows P-waves from the heart as detected and amplified by the atrial sensing amplifier. In the portion of the chart shown in FIG. 3, five P-wave occurrences are shown. For purposes of illustration, the first P-wave results in atrial synchronous pacing mode of operation. Specifically, the occurrence of the first P-wave initiates the A-V delay interval timer, which in the example shown, is 175 milliseconds. At the end of that time the ventricular stimulation pulse is delivered. At the same time the atrial sense amplifier is blanked or refractory for approximately 125 milliseconds, and the upper and lower rate timers are reset.

The upper rate limit timer is set at 343 milliseconds, corresponding to an upper heart rate of 175 bpm, which means that the circuit is ready to deliver a stimulus (in response to a P-wave) at the end of the high rate limit timing period of 343 milliseconds, such as might occur in the case of the patient exercising at a high heart rate. However, any A-V timer output occurring sooner than the time-out of the upper rate limit timer would simply be delayed until the time-out, and the ventricular stimulation would be delivered at that point. This accounts for the shape of the curve of FIG. 2 beyond the 175 beat per minute upper rate limit. In that region fast P-waves are detected but the corresponding ventricular pulses are delayed by the upper rate limit timer in order to keep the beat-to-beat rate at the 175 beat per minute upper limit. Due to the delaying action some P-waves are blocked. The instantaneous pacing rate is at or below the upper rate limit. However, since some P-waves are blocked the average rate has the characteristics shown in FIG. 2. This type of upper rate limit behavior is explained further in U.S. Pat. No. 4,059,116 by John M. Adams, which is assigned to the assignee of the present patent.

Returning to the example of FIG. 3, the first P-wave resulted in delivery of a ventricular stimulus with atrial synchrony. Assume now however that the patient's spontaneous atrial rate is low, at approximately 1,100 milliseconds escape interval, which corresponds to approximately 54.5 beats per minute. Therefore, on the second P-wave of FIG. 3 the A-V interval is initiated, but before it can time out, the low rate limit timer of 1,000 ms times out and causes a ventricular stimulation pulse. This is repeated for the next three ventricular stimulation pulses in the example shown. In each case the P-wave interval is too slow, so pacing at the 60 beat per minute rate takes place.

The top two lines of FIG. 3 show the dissociation between the operation of the atrium and ventricle during this low rate limit backup mode. The P-wave and the ventricular stimulation pulse are not in synchrony and are operating at different frequencies. This causes the P-wave to drift through the ventricular stimulation pulse, as viewed in time through each successive cycle. Eventually, the P-wave will fall, in relationship to the ventricular stimulation pulse, at a time just after the end of the atrial refractory period. This is shown in FIG. 3 at the fifth P-wave. This initiates an A-V time interval, and the end of that interval falls still slightly within the time interval of the upper rate limit timer, so the ventricular pulse is delayed until the time-out of the upper rate timer. For an upper rate limit of 175 beats per minute, the result is the delivery of a closely coupled ventricular stimulating pulse only 343 milliseconds from the preceding pulse.

This closely coupled pulse unfortunately may fall in the vulnerable period of the ventricles, during repolarization from the previous contraction. This can be dangerous and in certain circumstances may lead to ventricular fibrillation. Also, the electrocardiogram of a patient having this type of pacemaker may be confusing and may be easily misinterpreted as a malfunctioning pacemaker because of the closely coupled pulse occurring in the middle of otherwise normally spaced pulses.

It is apparent from studying the sequence of events involving the fifth P-wave of FIG. 3, that the unwanted close coupling between the ventricular stimulating pulses may be alleviated by increasing the time-out interval of the upper rate limit timer. This would have the effect of delaying, or moving to the right in FIG. 3, the final stimulation pulse shown, so as to move it outside the vulnerable period. However, to do so would lower the upper rate limit to where the pacemaker could not track P-waves occurring faster than perhaps 100 beats per minute. This would severely compromise the usefulness of the pacemaker, as pacemakers of this type are frequently used with patients capable of heart rates of 150 or above during exercise. Under those circumstances synchrony would be lost at a low rate and the device would be providing less physiological benefit.

DETAILED DESCRIPTION OF THE INVENTION

Both of the above unwanted effects are avoided in the present invention. In FIG. 4, reference number 10 again designates a heart, having an atrial lead 11 with an electrode 12 therein, and a ventricular lead 14 with electrode 15 positioned therein. Lead 11 connects to terminal 13 and lead 14 connects to ventricular terminal 16.

Inside the pacemaker, atrial terminal 13 connects to the input of atrial sensing amplifier and detector 20 which functions to detect P-waves indicative of atrial contractions. Atrial sense amplifier 20 sends signals over conductor 21 to the start input of the A-V delay timer 22. Unless reset by a signal applied to its reset input from conductor 41, timer 22 provides a triggering pulse at its trigger output at the A-V delay interval following receipt of a start signal from conductor 21. This trigger signal is applied over conductor 23 to the upper rate limit control circuitry which is described in detail below.

The ventricular terminal 16 connects via conductor 31 to the output of a output pulse generating circuit 30 which functions, as is known in the prior art, to generate the ventricular stimulating pulses. Generator 30 generates its pulses in response to ventricular pace or atrial trigger signals applied to its input over conductor 32. A branch of conductor 31 connects to the ventricular sensing amplifier and detector 40, which functions to produce signals at its output on conductor 41 indicative of ventricular events, i.e., either a ventricular contraction or a ventricular stimulation pulse.

Both atrial sensing amplifier 20 and ventricular sensing amplifier 40 have circuit means for providing refractory periods for the sensing amplifier following detection of sensed atrial or ventricular events, respectively. In the preferred embodiment the atrial amplifier is rendered inoperative upon occurrence of an atrial or ventricular event, and it remains refractory during the refractory period of the ventricular amplifier and for an overlap period thereafter. The preferred embodiment uses the atrial refractory control as disclosed in my copending patent application entitled "PACEMAKER ATRIAL REFRACTORY CONTROL FOR R-WAVE REJECTION."

A branch of conductor 41 connects to the reset input of lower rate timer 42. Timer 42 functions to produce a signal at its output on conductor 43 at the end of its time-out interval corresponding to the lower, ventricular backup rate escape interval.

A program control circuit 50 is provided which operates in the manner known in the art to receive control signals in the form of rf energy transmitted from outside the body and received by antenna 51. Controller 50 decodes and processes the received rf signals to send program signals to timer 22 via data bus 52; to the lower rate timer 42 via data bus 53; and to the upper rate limit control via data bus 54. Although single lines are shown in the drawing for purposes of clarity, it will be appreciated that the program signals to the three timing circuits preferably take the form of digital control words, and thus data buses 52, 53, and 54 may comprise several parallel data lines to convey the digital control signals for programming the intervals. By means of the program control circuitry, one of several possible time delays can be selected for timer 22, as may be appropriate for the patient. Similarly, the upper and lower beat per minute rate values can be selected as appropriate for a given individual.

Within the upper rate limit control or triggering coupling circuit is an upper rate limit timer 60 which receives start signals over conductor 61 from OR gate 62. Timer 60 provides a time-out signal at its output at lead 63, at the end of the upper rate interval, for example 343 milliseconds in the case of an upper rate limit of 175 beats per minute. Conductor 63 connects to one input of an AND gate 64, the other input of which is connected to conductor 23. The output of AND gate 64 connects via conductor 65 to one input of an OR gate 70, and to the reset input of a flip flop 71.

A branch of conductor 41 connects to one input of OR gate 62, and a branch of conductor 43 connects to its other input. A branch of conductor 43 also connects to an input of OR gate 70, and to the set input of flip-flop 71.

Data bus 54 connects to a plurality of AND gates 72a through 72n. The exact number of gates corresponds to the number of parallel bits of the program information, but for purposes of clarity only the least and most significant bits are shown in the drawing. The other inputs to gates 72a through 72n connect via conductor 73 to the Q output of flip flop 71. The outputs from AND gates 72a through 72n connect over leads 74a through 74n to inputs of OR gates 75a through 75n. Again the number of OR gates corresponds to the number of bits in the digital control for the timer program value. The output of these OR gates connect through conductors 76a through 76n to the program inputs for upper rate timer 60.

A circuit 80 is provided to generate an output digital control word corresponding to a time rate interval of 100 beats per minute, which corresponds to an escape interval of 600 milliseconds. This control word is outputted on conductors 81a through 81n which connect to inputs in AND gates 82a through 82n. The outputs of these gates conduct via conductors 83a through 83n to the other inputs of OR gates 75a through 75n. The other inputs to AND gates 82 connect from the Q output of flip flop 71 by conductor 84.

In operation in normal atrial synchronous mode, (corresponding to the 60 through 175 beat per minute range of FIG. 2) P-waves are detected by sense amplifier 20 and start timer 22. At the end of the A-V delay interval, a triggering pulse is emitted at conductor 23 which will couple through AND gate 64 and OR gate 70 to pulse generator 30, causing it to generate and deliver a ventricular stimulation pulse. This sequence assumes that the upper rate timer 60 would have timed out its interval prior to the triggering pulse on conductor 23, which of course would be the case in the above-mentioned one to one region of the operating curve of FIG. 2. In the case of atrial synchronous operation at a rate in excess of the upper rate limit, the triggering signal 23 is presented by timer 22, but it is held at gate 64 until timer 60 completes its time-out interval, after which time the triggering signal is gated to cause generator 30 to deliver its output pulse. In that manner upper rate timer 60 serves to prevent delivery of pacing pulses at a rate in excess of the program value.

When the triggering pulse is transmitted through conductor 65 to gate 70 and generator 30, it also resets flip flop 71. This enables gates 72 and disables gates 82, so that the upper rate limit interval applicable for timer 60 is the program value from program control 50.

Occurrence of either a ventricular stimulation pulse or a natural ventricular contraction is detected by circuit 40, which transmits a signal on conductor 41 to reset timers 22 and 42, and restart timer 60.

Operation of the circuit of FIG. 4 in the lower rate ventricular backup mode is as follows. If a ventricular event does not occur prior to the time-out of the lower rate timer 42, an output pulse will be generated. For example, assuming that the programmed value for timer 42 is 1,000 milliseconds, corresponding to a pacing rate of 60 beats per minute, timer 42 will send a signal over lead 43 through gate 70 to generator 30, causing it to deliver an output stimulating pulse when timer 42 times out. Another pulse will be caused by timer 42 1,000 milliseconds later, unless prior to that time, either a spontaneous ventricular contraction takes place, or a ventricular stimulus is emitted caused by the control path including atrial amplifier 20, delay timer 22, and gate 64.

At the same time that lower rate timer 42 causes generator 30 to deliver an output pulse, the signal on conductor 43 sets flip flop 71. This in turn provides a signal on conductor 84 from the Q output to enable gates 82a-82n, and a signal on conductor 73 to disable gates 72a-72n. This switching of flipflop 71 gates the code for a 100 beat per minute rate from device 80 into the program inputs of timer 60. Upper rate timer 60 will remain programmed for the 100 bpm-600 ms escape interval timing as long as pacing of the heart is under control of the lower rate timer 42. When atrial synchrony is regained and a pacing signal is transmitted through conductor 65 to the output circuit, flip flop 71 is reset and the 100 bpm-600 ms timing is removed and the program upper rate limit from data bus 54 is gated into upper rate timer 60.

Figure 5:
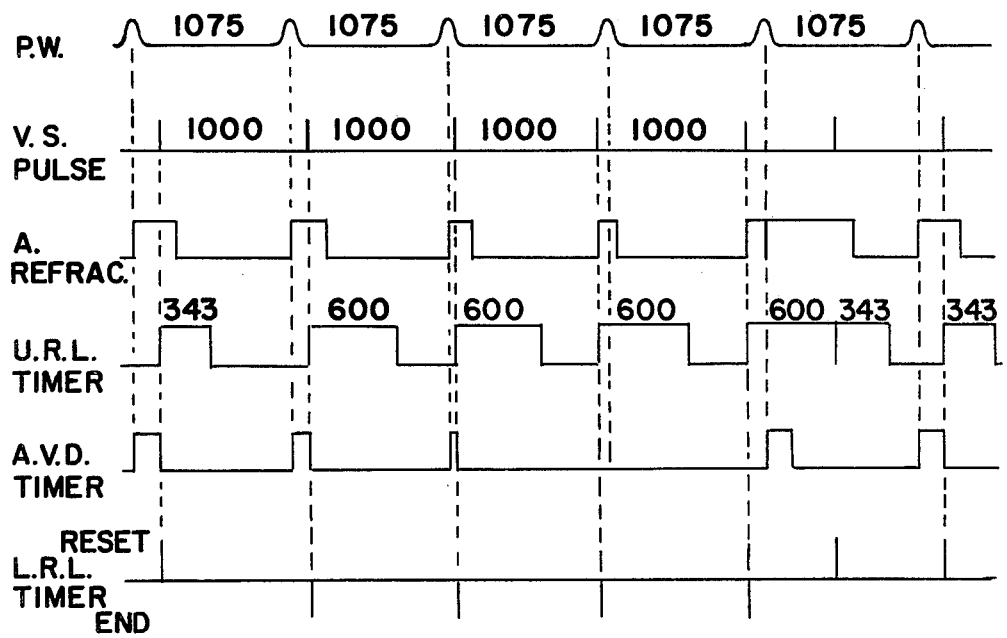
FIG. 5 is a timing chart showing the operation of the pacemaker of FIG. 4 according to the present invention in solving the problem of closely coupled stimulating pulses.

The operation of the pacemaker of FIG. 4 in overcoming the problem of closely coupled ventricular pulses that exists in the prior art will be seen with the aid of FIG. 5. In FIG. 5, the horizontal axis again represents time and the six heart and pacemaker parameters that were labeled in FIG. 3 are also shown in FIG. 5, but for the operation of the circuit of FIG. 4. For illustrative purposes, the first P-wave and ventricular stimulation pulse show atrial synchronous mode of pacing. However, the next several pulses show pacing at the lower ventricular backup rate. This is because the P-waves are occurring with escape intervals of approximately 1,075 ms, which is roughly 56 bpm, a slower rate than the programmed 60 bpm-1,000 ms escape interval for the lower rate timer. Accordingly, the second, third, fourth, and fifth ventricular stimulation pulses are delivered at 1,000 ms intervals, and the P-waves and ventricular stimulation pulses become dissociated, with the P-wave drifting through the ventricular stimulation pulse time. On the fifth P-wave of FIG. 5, the P-wave occurs just after the end of the refractory period of the atrial sensing amplifier following the ventricular stimulation pulse. It will be recalled that in the case of the prior art of FIG. 3, this situation resulted in the delivery of the closely coupled second ventricular pulse, separated from the preceding pulse by only the upper rate limit escape interval of 343 ms. However, the invention of FIG. 4 solves this problem because the upper rate limit timer has been switched to a lower upper rate of 100 bpm-600 ms escape interval.

This is seen in FIG. 5 wherein the upper rate timer times out a short 343 ms interval on the first cycle which was triggered through the atrial sensing path. The second heartbeat cycle shown was triggered by the lower rate timer and the flip flop 71 was set to switch the program value for timer 60. Therefore on the second, third, fourth and fifth cycles shown in FIG. 5, the ventricular time-out rate is switched to the 100 bpm-600 ms interval. Therefore, on the fifth cycle where the P-wave occurs immediately after the refractory period of the atrial amplifier, the A-V delay timer is triggered and times out, but gate 64 delays the delivery of a pace pulse to the output circuit until the end of the time-out period of timer 60 which is at the 600 millisecond level. At 600 milliseconds following the last ventricular stimulation pulse, the trigger signal is passed through to the output and a further ventricular pulse is delivered. It will be seen that the sixth ventricular pulse in FIG. 5, although more closely coupled to the fifth than the preceding pulses, is still separated by sufficient time to avoid having the pulse fall in the vulnerable period of the heart. Thus the problem of closely coupled pulses falling in the vulnerable period is eliminated.

Since the sixth ventricular stimulation pulse shown in FIG. 5 was the result of triggering through the atrial path, flip flop 71 is reset and the normal upper rate limit of 175 bpm-343 ms is restored. In the final heartbeat cycle shown in FIG. 5, atrail synchrony is regained and the ventricular stimulation pulse is delivered in synchrony following detection of the P-wave, and the shorter upper rate timer time-out period is applicable. With the upper rate timer in its normal program mode, the pacemaker is ready to track P-waves of the heart at a high rate up to the programmed limit, while still being capable of switching to the lower upper rate limit in the event of ventricular backup pacing, in order to prevent closely coupled ventricular pulses from falling in the vulnerable period of the heart.

What is claimed:

1. A heart pacemaker having atrial synchronous and minimum rate ventricular pacing modes and including means for preventing closely coupled ventricular stimulation pulses, comprising:

atrial terminal means and ventricular terminal means for connection, respectively, to the atrium and ventricle of a patient's heart;
   output pulse generating means for selectively delivering ventricular electrical stimulation pulses to said ventricular terminal means;
   ventricular sense amplifier means connected to said ventricular terminal means for sensing ventricular beats of the heart and for producing a corresponding ventricular signal;
   atrial sense amplifier means connected to said atrial terminal means for sensing atrial contractions of the heart and for producing a corresponding atrial signal;
   control means connected to receive said atrial and ventricular signals and connected to control said output pulse generating means, said control means for causing delivery of delayed synchronized ventricular stimulation pulses in response to atrial signals occurring faster than a predetermined minimum rate, and for causing delivery of ventricular stimulation pulses to maintain the ventricular rate at the predetermined minimum rate in the absence of atrial signals above the minimum rate; and
   said control means including means for preventing delivery of a ventricular stimulation pulse at a pacing rate in excess of a predetermined maximum rate limit with respect to a proceding spontaneous or stimulated ventricular contraction, and further including means for increasing said predetermined maximum rate limit during atrial synchronous pacing and reducing to a lower maximum rate limit when pacing at said predetermined minimum pacing rate.

2. A pacemaker having atrial synchronous and minimum rate ventricular backup pacing modes and a triggering coupling circuit for preventing closely coupled ventricular stimulation pulses comprising:

ventricular terminal means for connection to a patient's heart for delivering ventricular stimulation pulses thereto;
   pulse generating means for selectively delivering ventricular electrical stimulation output pulses to said ventricular terminal means;
   ventricular sense amplifier means connected to said ventricular terminal means for sensing ventricular beats of the heart;
   atrial terminal means for connection to a patient's heart;
   atrial sense amplifier means connected to said atrial terminal means for sensing atrial contractions;
   delay timer means operatively connected to said atrial sense amplifier means and operatively connected to said pulse generating means for causing generation of atrial synchronous output pulses after a predetermined time interval following sensed atrial contractions;
   minimum rate control means operatively connected to said ventricular sense amplifier means and said pulse generating means for causing delivery of output pulses at a predetermined minimum pacing rate in the absence of atrial synchronous pacing at a higher rate;
   maximum rate control means operatively associated with said delay timer means and said generating means for preventing delivery of any output pulse within a predetermined minimum escape interval from a previous ventricular contraction or stimulation pulse;

means for increasing said predetermined minimum escape interval for said maximum rate control means during minimum rate pacing by said pacemaker.

3. A pacemaker having atrial synchronous and minimum rate ventricular backup pacing modes and a triggering coupling circuit for preventing closely coupled ventricular stimulation pulses comprising:

ventricular terminal means for connection to a patient's heart for delivering ventricular stimulation pulses thereto;

pulse generating means for selectively delivering ventricular electrical stimulation output pulses to said ventricular terminal means;

ventricular sense amplifier means connected to said said ventricular terminal means for sensing ventricular beats of the heart;

atrial terminal means for connection to a patient's heart;

atrial sense amplifier means connected to said atrial terminal means for sensing atrial contractions;

atrial-ventricular delay timer means operatively connected to said atrial sense amplifier means and operative to produce an output triggering signal delayed according to a selected atrial-ventricular delay interval, in response to a sensed atrial contraction;

gating means for selectively transmitting said output triggering signal to said pulse generating means for causing the generation of a ventricular electrical stimulation pulse;

a maximum rate limit timer operatively connected to said gating means for preventing transmission of said output trigger signal during its time-out interval;

a minimum rate limit timer including means for delivering a pace signal to cause said pulse generating means to deliver a ventricular electrical stimulation pulse at the end of the time-out interval of said minimum rate limit timer;

means for starting and resetting said minimum and maximum rate limit timers upon delivery of a ventricular electrical stimulation output pulse; and means for selectively changing the time-out interval of said maximum rate limit timer to a first time-out interval upon delivery of an output stimulating pulse in response to an output trigger signal from said atrial-ventricular delay timer, and to a second time-out interval longer than said first time-out interval, upon delivery of an output electrical stimulation pulse in response to a pace signal from said minimum rate limit timer.

4. A pacemaker according to claim 3 wherein said maximum rate limit timer comprises a programmable timer, and wherein said means for selectively changing includes a bistable circuit operated in response to an output trigger signal from the atrial-ventricular timer delay timer or a pace signal from said minimum rate limit timer, and program gating means operable in response to said bistable circuit for selectively gating program signals to said programmable timer corresponding to said first and second time-out intervals.

5. A pacemaker control circuit for use in a heart pacemaker having ventricular sensing, atrial sensing and ventricular output pulse circuits, said pacemaker control circuit having atrial synchronous and minimum rate ventricular pacing modes and including means for preventing closely coupled ventricular stimulation pulses, comprising:

input means for receiving ventricular signals and for receiving atrial signals from said ventricular and atrial sensing circuits respectively;

control means responsive to said signals for selectively causing said output pulse circuit to deliver ventricular output pulses, said control means for producing delayed synchronized output pulses when said atrial signals occur faster than a predetermined minimum rate, and for producing output pulses to maintain the ventricular rate at the predetermined minimum rate in the absense of atrial signals above the minimum rate; and said control means including means for preventing delivery of an output pulse at a pacing rate in excess of a predetermined maximum limit with respect to a preceeding spontaneous or stimulated ventricular contraction, and further including means for increasing said predetermined maximum rate limit during atrial synchronous pacing and reducing to a lower maximum rate limit when pacing at said predetermined minimum pacing rate.

6. A pacemaker control circuit, for use in a heart pacemaker having ventricular sensing, atrial sensing and ventricular output pulse circuits, said pacemaker control circuit having atrial synchronous and minimum rate ventricular backup pacing modes and a triggering coupling circuit for preventing closely coupled ventricular stimulation pulses, comprising:

delay timer means operatively connected to said atrial sensing circuit and operatively connected to said ventricular output pulse circuit for causing generation of atrial synchronous output pulses after a predetermined time interval following sensed atrial contractions;

minimum rate control means operatively connected to the ventricular sensing circuit and said ventricular output pulse circuit for causing delivery of output pulses at a predetermined minimum pacing rate in the absense of atrial synchronous pacing at a higher rate;

maximum rate control means operatively associated with said delay timer means and said ventricular output pulse circuit for preventing delivery of any output pulse within a predetermined minimum escape interval from a previous ventricular contraction or stimulation pulse; and means for increasing said predetermined minimum escape interval for said maximum rate control means during minimum rate pacing by said pacemaker.

7. A pacemaker control circuit for use in a heart pacemaker having ventricular sensing, atrial sensing and ventricular output pulse circuits, said pacemaker control circuit having atrial synchronous and minimum rate ventricular backup pacing modes and a triggering coupling circuit for preventing closely coupled ventricular stimulation pulses comprising:

atrial-ventricular delay timer means operatively connected to said atrial sensing circuit and operative to produce an output triggering signal delayed according to a selected atrial-ventricular delay interval, in response to a sensed atrial contraction;

gating means for selectively transmitting said output triggering signals to said output pulse circuit for causing the generation of a ventricular output pulse;

a maximum rate limit timer operatively connected to said gating means for preventing transmission of said output trigger signal during its time-out interval;

a minimum rate limit timer including means for delivering a pace signal to cause said pulse generating means to deliver a ventricular electrical stimulation pulse at the end of the time-out interval of said minimum rate limit timer;

means for starting and resetting said minimum and maximum rate limit timers upon deliver of ventricular output pulse; and means for selectively changing the time-out interval of said maximum rate limit timer to a first time-out interval upon delivery of an output stimulating pulse in response to an output trigger signal from said atrial-ventricular delay timer, and to a second time-out interval longer than said first time-out interval, upon delivery of a ventricular output pulse in response to a pace signal from said minimum rate limit timer.

* * * * *